(12) United States Patent
Mershon

(10) Patent No.: US 7,303,759 B2
(45) Date of Patent: Dec. 4, 2007

(54) COMPOSITIONS AND METHODS FOR REDUCING BLOOD AND FLUID LOSS FROM OPEN WOUNDS

(75) Inventor: Millard Marsden Mershon, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 118 days.

(21) Appl. No.: 10/178,448

(22) Filed: Jun. 20, 2002

(65) Prior Publication Data

US 2003/0008011 A1 Jan. 9, 2003

Related U.S. Application Data

(60) Provisional application No. 60/300,384, filed on Jun. 22, 2001.

(51) Int. Cl.
*A61F 13/00* (2006.01)
*A61K 9/70* (2006.01)
*A61L 15/16* (2006.01)

(52) U.S. Cl. .................... 424/443; 424/449; 424/448

(58) Field of Classification Search ............... 424/443, 424/449
See application file for complete search history.

(56) References Cited

U.S. PATENT DOCUMENTS

| | | | | |
|---|---|---|---|---|
| 4,552,138 | A * | 11/1985 | Hofeditz et al. | 604/304 |
| 4,822,349 | A | 4/1989 | Hursey et al. | 424/445 |
| 4,920,158 | A * | 4/1990 | Murray et al. | 523/111 |
| 5,260,066 | A * | 11/1993 | Wood et al. | 424/447 |
| 5,457,093 | A * | 10/1995 | Cini et al. | 514/12 |
| 5,578,661 | A * | 11/1996 | Fox et al. | 524/27 |
| 5,858,350 | A | 1/1999 | Vournakis et al. | 424/93.1 |
| 5,891,074 | A * | 4/1999 | Cesarczyk | 602/42 |
| 6,060,461 | A | 5/2000 | Drake | 514/54 |
| 6,133,326 | A | 10/2000 | Mayne | |
| 6,187,347 | B1 | 2/2001 | Patterson et al. | 424/646 |
| 6,399,092 | B1 * | 6/2002 | Hobson et al. | 424/443 |
| 6,531,500 | B2 * | 3/2003 | Farber | 514/390 |
| 6,559,350 | B1 | 5/2003 | Tetreault et al. | 602/42 |
| 6,723,781 | B1 * | 4/2004 | Frate et al. | 524/522 |

OTHER PUBLICATIONS

Clinical Studies: FirstSTOP, by VasoSeal, from internet website http://www.vasoseal.com/sh/shclinical.html, 2001.
Catrix Wound Dressing, by Catrix Science & Nature, from internet website http:///www.catrix.com/products/wound_dressing/html., 1997.
Ferber et al., "Case Report: Interactive wet therapy with TenderWet—three years clinical experience with chronic wounds", published at internet website http://www.hartmann-online.de/english/produkte/wunderbehandling/wunderforum/4-95-2.html, Apr. 4, 1995 (6 pages).
Kocak et al., "Comparative Efficacy of Topical SodiumHyaluronate in Renal Trauma Model", published at internet website http://www.brazjurol.com.br/maio_2001/Kocak_289_294.html, 2001 (6 pages).
PR Newswire Magazine, "Focal, Inc. Receives U.S. Government Grant to Study Use of FocalSEal Technology in Carpal Tunnel Surgery", published at internet website http://www.findarticles.com/cf_o/m4PRN/1998?Sept/21/53.../article.html, Sep. 21, 1998 (2 pages).
Hemaseel APR, Haemacure Products, published internet website http://www.haemacure.com/en/products/hemaseelAPR.html, referencing product launch in June of 1998 (1 page).
"Closure Medical closes distribution deal," The Business Journal, published at internet website http://trangle.bizjournals.com/trinalge/stories/2001/07/16/daily13.html, Jul. 17, 2001 (2 pages).
Johnson & Johnson, News, "Johnson & Johnson Has You Covered—Presenting Three New Bandages to Protect Wounds", published at internet website http://www.jnj.com/news/jnj_news/20020308_1047.html, Mar. 12, 2001 (2 pages).
"Closure Medical Corporation (CLSR) Signs Definitive Agreement with Johnson & Johnson Companies, Inc. For Its Liquiderm Liquid Adhesive Bandage", published at internet website http://www.biospace.com/ccis/news_story.cfm, May 29, 2001 (2 pages).
Notice in Popular Science Magazine, Jun. 2001, "Blood is Thicker with Seawater", p. 14.
Sugg, Diane, "Bandage stanches bleeding in seconds", published in The Sun, Saturday edition, Oct. 17, 1998, pp. 1A and 5A.
International Search Report for International patent application No. PCT/US02/19554 (filed Jun. 20, 2002) (parallel PCT case to instant US case), dated Feb. 26, 2003 (2 pages).

* cited by examiner

*Primary Examiner*—Isis Ghali
(74) *Attorney, Agent, or Firm*—Elizabeth Arwine

(57) ABSTRACT

The invention described herein relates to methods for reducing and/or stopping bleeding or fluid loss from open wound, denuded tissue, or burned skin, comprising the step of applying to the open wound, denuded tissue or burned skin a gel-forming composition comprising at least one of the following compositions: a polyacrylic acid having the structural formula $[CH_2=CHCO_2H]_n$, where n is between 10,000 and 70,000; a polyacrylic acid and a desiccated water soluble organic or inorganic base; polyacrylic acid and a desiccated poorly soluble basic salt, and a polyvinyl alcohol having the structural formula of $[CH_2=CHOH]_n$, where n is between 15,000 and 150,000. When the gel-forming composition is applied to the open wound, denuded tissue, or burned skin, its ions react therein in the presence of water from blood or body fluid therein to form an aqueous gel or mucilage having sufficient viscosity and adhesiveness to cover and adhere to the open wound, denuded tissue, or burned skin so that bleeding or fluid loss is thereby reduced and/or stopped.

44 Claims, No Drawings

US 7,303,759 B2

COMPOSITIONS AND METHODS FOR REDUCING BLOOD AND FLUID LOSS FROM OPEN WOUNDS

This application claims priority benefit to provisional application Ser. No. 60/300,384, filed Jun. 22, 2001.

FIELD OF THE INVENTION

This invention comprises a new method of use, and physiologically and medically acceptable compositions of matter having relatively low-cost; these provide hemorrhage and injury control comprising artificial clotting of blood, protective sealing of body surfaces with normal, damaged or destroyed skin, and temporary adhesion to or between such body surfaces. This invention further comprises new and useful compositions of matter, and applications thereof that use water, as found in blood and other body fluids, to activate the formation of artificial clots that can adhere to wounded tissue for the suppression of fluid loss and/or the protection of viable cells.

BACKGROUND OF THE INVENTION

Innumerable lives have been lost to hemorrhage, escape of tissue fluids from burned or denuded body surfaces, and infections or toxic effects consequent to contamination of open wounds. Accordingly, a variety of methods have been used to stop or control losses of blood or fluids and imitate defensive functions of intact skin. Heavy bleeding may be controlled in many cases if large vessels can be flattened. This may be done by transfer of external pressure through adjacent tissue or bandaging material. If less severe injuries require surgical care, "first aid strips" or similar non-adhesive bandages may limit minor hemorrhage and prevent wound contamination.

Unfortunately, severe injuries and burns often exceed the capabilities of first aid bandages. Some injuries exceed the capabilities of all bandages and care available at the site of injury. Victims frequently bleed to death before they can benefit from care by highly trained and superbly equipped surgeons who might save them. It is known that hemorrhage is the cause of many battlefield deaths and increases the morbidity of surviving casualties. An effective method for controlling hemorrhage in forward treatment elements (pre-hospital, non-physician providers) would greatly reduce combat mortality rates and decrease logistical requirements for combat casualty care. To meet U.S. Army requirements, ". . . a topical hemostatic agent must control rapidly flowing, otherwise lethal, large venous or arterial hemorrhage, through a pool of blood—without vascular control." Hemorrhage control poses similar life-threatening problems with non-military personnel.

Relatively minor injuries, such as a superficially cut finger or scraped knee, are often covered with sterile cotton gauze pads that are held over the injured site by pressure from an adhesive barrier strip affixed to adjacent normal skin. Such first aid strips may be used to sequester small amounts of blood within the absorbent pad until components of blood and damaged tissue can form a fibrin-based clot. The clot initially clogs the ends of small blood vessels and adheres to wounded surfaces. When large vessels are cut or torn, the rapid flow of escaping blood tends to remove fibrin clots before they can clog the vessel and adhere to the adjacent damaged tissue. There is a requirement for material able to arrest such major hemorrhage.

In many cases, blood adhering to damaged tissue is clotted and slowly transformed into a scab that serves as a skin substitute; it retains body fluids while sealing out bacteria and other environmental hazards. Wound healing normally takes place under cover of the protective scab, which prevents drying of underlying cells and undesirable inflammatory reactions that limit normal healing. Such healing requires closure of any void with fibroblasts and the migration of epidermal cells over fibroblasts and fibroblastic collagen products under physiological conditions. There is a need for methods able to rapidly provide the protective functions normally provided by epithelial cells and to foster re-epithelialization for re-establishment of such functions. An artificial scab is expected to provide such immediate protection but it may also be used to prevent or retard possibly disfiguring scar formation.

Military organizations have found it difficult to protect human skin against some chemical warfare agents. These include GB (isopropyl-methylphosphonofluridate), GD (1,2, 2-trimethylpropyl methylphosphonofluridate) and VX (o-ethyl S-[2-(diisopropylamino)ethyl]methylphosphonothiolate), each an anticholinesterase "nerve agent", vesicants such as HD (bis-2-chloroethyl sulfide) and its close relative that is known as sesquimustard, "tear gas" irritant/vesicants such as CS (o-chlorobenzylidene malononitrile) and CN (chloracetophenone), and various psychotomimietics such as BZ and EA3580 (anticholinergic agent prototypes). For instance, the need for skin protection against liquid mustard agents was recognized during World War I. Accordingly, several ointments or creams (topical skin protectants) were developed to shield skin from contamination with toxic chemical warfare agents. Some of these protectants incorporated detoxifying components, thickeners, and camouflage pigments (example: M-5 ointment).

There are similar problems in protecting normal skin from noxious chemicals and the sealing of wounded tissues from exposure to infection and drying. Many "protective cream" products have been made and sold for the purpose of limiting access of noxious chemicals to skin. However, most incorporate lipophilic substances that have proven ineffective against the lipophilic chemical warfare agents. Skin exposure reduction paste against chemical warfare agents (SERPACWA), a mixture of non-wettable fluorocarbon compounds, is the only material approved by the U.S. Army and the Federal Food and Drug Administration for such protection. However, current instructions for its use state, "Do not apply SERPACWA to open wounds or remove bandages to apply SERPACWA to those areas." Further, many burn dressings and wound dressings provide protection for the damaged tissues, but none offer significant similarity to the properties of normal scabs that foster re-epithelialization.

There are a number of medical and non-medical applications that depend upon temporary adhesion between or to body surfaces. Some depend upon establishment of clean, dry surfaces. For example, first aid strips require such surfaces for attachment with a pressure-sensitive adhesive. Dental adhesives require a moist surface for attachment of dentures. Cyanoacrylate "tissue glues" react with very thin layers of water on normal skin or wounded tissue surfaces that can be placed in apposition. However, none of these adhesives is compatible with substantial amounts or depths of water or blood on a body surface. None are useful as soft tissue splints that stabilize torn tissue in the manner of bone fragment stabilization with splints.

Available adhesives lack hydrophilic properties optimal for product use as a vehicle for drugs to be absorbed from wounds, or on skin for retention of dermatological treatment substances intended to modify the stratum corneum. For instance, lipophilic adhesives and pharmaceutical vehicles adhere poorly to wet surfaces of wounds. They tend to retain lipophilic drugs (for example, vitamins A, D, and E that are known to promote wound healing) rather than facilitate their distribution into wounded tissue. In contrast, lipophilic materials readily tend to leave hydrophilic materials to enter lipophilic tissue membranes.

SUMMARY OF THE INVENTION

With the above circumstances and state of the art in mind, the inventor discovered new methods for suppression of massive blood or fluid loss and substitution for missing skin by inducing artificial clotting, based on water of blood or fluids, using compositions comprising anhydrous polymers such as polyacrylic acids of various chain lengths and modified monomer components. These are also known as carbomers or carboxypolymethylenes, and have been identified by trade names such as CARBOPOL or NOVEON. These are described as slightly acidic vinyl polymers with active carboxyl groups. Their linear polyacrylic backbones are cross-linked with various polyfunctional groups to create three-dimensional structures. For example, carbomer 934 P National Formulary (hereinafter denoted as NF), which is a crosslinked poly(acrylic acid) produced by Noveon, Inc. under the CAS number 9003-01-4, and has allyl sucrose cross-links; it is designated P for pharmaceutical grade and NF for listing in the National Formulary. Differing cross-links, molecular weight, and/or concentration in water support differing degrees of carbomer swelling in water. Such features can be varied to optimize properties for typical usage in medical and personal use products for which thickening, dispersion, emulsification, or suspension of solid ingredients may be desired. Product viscosities may be increased by use of inorganic or organic bases to neutralize and ionically cross-link carboxyl groups. Carbomers have been used for many years as low percentage ingredients to modify cosmetic lotions, creams and gels. More recently carbomer copolymers with variously hydrolyzed varieties of polyvinyl alcohol, polyvinyl acetate or polyvinyl pyrrolidone have been used as dry components of tablets. Carbomers or copolymers as sole or majority components are not generally known.

The polyacrylic acids contemplated for the compositions and methods of this invention have the representative monomeric chemical structure $[CH_2=CHCO_2H]_n$, where n is between about 10,000 and about 70,000. Other suitable anhydrous polymers include polyvinyl alcohols of various chain lengths and modified monomer components, including mixtures having the representative monomeric chemical structure $[CH_2=CHOH]_n$, where n is between about 15,000 and about 150,000.

The new method involves application of such compositions, preferably where the polymers are in finely divided form, directly onto wounded tissue. This invention is placed into operation when water from blood or serum is available to initiate formation of an artificial blood clot/adhesive polymer gel. Specifically, the polymers interact with water ($H_2O$) present in blood or body fluid in an open wound, denuded tissue or burned skin to form an aqueous gel or mucilage having sufficient viscosity and adhesiveness to cover and adhere to the open wound/denuded tissue/burned surface, so that bleeding or fluid loss is abated or stopped altogether. The desired properties of such gels are improved for specific applications by combining the anhydrous acidic polymers with a variety of alkaline or non-alkaline thickening agents and/or additives. Given finely divided and well mixed particles, contact with water facilitates ionic interactions that tend to increase gel viscosity. For example, neutralization of acid polymers occurs with use of compounds such as calcium hydroxide or magnesium hydroxide, and polyvinyl alcohol gels are thickened by borate salts. Use of a calcium salt improves fibrin-based clotting and gel formation. Use of a magnesium salt tends to impart rubbery characteristics and improve resistance to removal.

In addition, the inventor has found that certain embodiments of these methods are useful to protect skin or damaged tissues from penetration by harmful substances or organisms and to regulate water loss. In particular, the methods reduce skin exposure and penetration by chemical warfare agents and other chemicals that readily diffuse through hydrophobic materials used in conventional skin protective creams. Such materials are customarily used in skin creams to permit easy spreading, and resist wiping, washing, perspiration or rainwater. The materials of this invention are hydrophilic yet resistant to water, and resistant to wiping when cured with water, but they can be removed readily with physiological saline solution (for example, 0.85% sodium chloride in water) or stronger solutions containing calcium or magnesium ions. Removal may be aided by wiping with material ranging from cotton gauze to mechanical scrapers. Because the components and products are hydrophilic, they are resistant to wetting or penetration by hydrophobic chemical warfare agents and commonly found substances such as petroleum products.

Although anhydrous powered formulations are required for hemostasis, in general the compositions of this invention may be storage-stable, dry, liquid or paste-like comprising (a) one or more of the polyacrylic acid polymers or polyvinyl alcohol polymers described above, in one or more of their medically acceptable forms, with or without (b) one or more of the many moderately alkaline salts of calcium, magnesium and/or sodium, or other moderately alkaline organic salts or bases, in anhydrous or non-ionized form, with or without (c) being suspended in one of the hydrophilic, anhydrous, non-toxic liquids known to resist diffusion by lipophilic chemical warfare agents or environmental chemical hazards. Such liquids include but are not limited to polyoxyalkyene glycols, other substituted derivatives of glycol ($HOCH_2CH_2OH$), substituted derivatives of glycerol ($HOCH_2CHOHCH_2OH$), various nitrile silicone fluids, or miscellaneous anhydrous hydrophilic vehicles such as liquid surfactants. Compositions incorporating such liquids may be preferred to afford temporary protection of wounds or skin found at risk of exposure to contamination with chemical warfare agents, microbes, or other undesirable substances. When carbomers or copolymers are used to defend skin from chemical warfare agents, they are known as topical skin protectants. If similar compositions are optimized to keep chemical warfare agents out of open wounds, they are known as wound sealants.

The invention may entail use of storage-stable, dry, liquid or paste-like compositions with added minor amounts of other ingredients (preferably less than 10% of a final formulation) designed to enhance medical or military requirements for each final product. For example, one of the described dry or paste-like formulations might incorporate (a) one or more of the many antimicrobial compounds, (b) indicators able to detect toxic or infectious contamination, (c) microencapsulated or insoluble decontaminating reagents, (d) substances that double as detectors and detoxifiers, (e) a pH indicator, (f) a vasoconstrictive drug, (g)

camouflage pigment, and/or (h) a physical property modifier such as starch or another of the many non-toxic compounds which are known to be (or can be proven to be) safe for persistent contact with wounded or burned body surfaces.

Dry compositions are preferred for artificial clotting of blood or serum for immmediate hemostasis and supportive adhesive binding of damaged tissue (soft tissue splinting). Dry compositions are also preferred for creation of an artificial scab to hold clotted blood or tissue fluid components against the denuded wound surface. This arrangement permits viable epithelial cells at the wound perimeter to migrate over the denuded surface but under the protective artificial scab. Blends of dry and liquid components are preferred for use as topical skin protectants and as sealants to provide wounds with protection against chemical warfare agents and other contaminants. Dry materials (and dry materials suspended in anhydrous liquids) may be used to provide resistance to removal by wiping or washing (as with topical medicaments or cosmetics) or both wiping or washing (as by licking during veterinary use).

Compositions of the invention are advantageous for the following reasons. First, they provide superior sealing in that they offer more properties of normal skin than other skin substitutes (i.e., the other compositions and methods use either hydrophobic or porous materials). Further, the compositions may be much less expensive by comparison with hemostatic compositions derived from human or animal blood components or from other natural sources. They may form surfaces much more resistant to transit by toxic chemicals, xenobiotics, infectious agents, or excess moisture and oxygen, by comparison with other polymeric compositions or bandaging. In addition, they may be easier to store, carry in the field for instant use, and keep usable without refrigeration or special packaging by comparison with natural products. They may provide more substance for the stabilization of field wounds and reinforcement of bandages than alternatives. They may be more useful than alternatives currently used in hospitals (as semi-permeable dressings on burned or otherwise denuded surfaces) to promote healing. They may be used to better minimize wound contractures and scarring by comparison with currently available surgical supplies. Further, they may better serve uniquely military functions, such as co-formulation with (or under coatings of) reagents used for chemical or biological agent detection, wound decontamination, temporary topical skin protection, and/or field camouflage of casualties, as compared with known alternatives.

For instance, as an advantage over the lipophilic adhesives available currently, the compositions of this method adhere well to the wet surfaces of open wounds. Further, the hydrophilic formulations of this method can be expected to become adherent to skin via water associated with stratum corneum so that lipophilic substances would tend to distribute favorably into the lipophilic substances of stratum corneum. Such favorable properties may be realized whether the drug-containing formulation is applied as a powder or as a paste made with one of the anhydrous, hydrophilic, chemical agent-resistant liquids mentioned above.

In addition, other advantages these methods have over previous methods include:

A. The use of an alkaline compound for thickening of a wetted polymer permits alkaline hydrolysis of some chemicals (for example: GB, GD and CS) that might otherwise penetrate skin or a persistently exposed polymeric coating over skin or a wound.
B. Use of a hydrophilic medium and active ingredients that are hydrophilic results in poor solubility of several skin penetrants (for example GB, GD, VX, vesicant agents, CS, CN, and psychotomimetic agents) in the material. Experimental results suggest that incorporation of as little as 1% of any of several common lipophilic ingredients of other "skin protectant creams" will create diffusion pathways for passage of chemical warfare agents. Petrolatum, lanolin, and silicone greases are examples of such materials, which are diverse and numerous.
C. All components of these mixtures are non-toxic except sodium borate (as used to thicken polyvinyl alcohol mucilages), which has a low toxicity. Mixtures can be buffered to the desired pH for compatibility with wounded tissue or intact skin.
D. Water cured coatings have been shown to be sufficiently insoluble to resist wiping for five minutes with 5.25% sodium hypochlorite bleach solution. Such results suggest that other strong decontaminating materials could be applied over such coatings on skin. Therefore, it follows that skin may be protected both from the hazardous agent and the effects of a decontaminant that might be used to remove a hazardous liquid anti-cholinesterase, vesicant, or other chemical warfare agent.
E. Antibiotics and/or other medicaments can be incorporated into modified formulations intended for wound or burn dressings to provide intimate, continuous contact with the damaged tissue, and a more favorable distribution into wet tissue than most creams provide.

In general, the compositions of the invention have properties, features and results including the following:

A. They use water of blood to trigger hemostatic response.
B. They immediately initiate blood element stasis without the delay involved in fibrin-based clotting.
C. They stop the flow of blood of patients previously treated with anti-clotting agents such as coumadin.
D. They stop the flow of blood of patients that lack blood clotting factors (such as hemophiliacs).
E. They are fixed by water from skin or wound, with no need for evaporation of water or solvent.
F. They are hydrophilic yet water resistant.
G. They are easy to spread yet resistant to wiping when cured.
H. They are uniquely resistant to penetration by substances that penetrate skin readily.
I. They permit use of mild alkali on skin in a protective coating as an aid to alkaline hydrolysis of certain chemical warfare agents (e.g.: GB, GD, CS).
H. They support use of a non-ionic anhydrous hydrophilic liquid to maintain dispersion of materials able to react in the presence of water from the skin.
I. They are able to absorb additional perspiration after curing so that plasticizing occurs rather than blistering of the protective film
J. They are able to lose moisture by evaporation to permit body cooling.
K. They can act as a buffer between tissue and atmosphere to prevent excessive tissue dehydration (or hydration, if the environment is water).
L. They act as a buffer between tissue and atmosphere to prevent excessive tissue oxygen exposure leading to free radical formation and oxidative damage to tissue.
M. They can be made to absorb $CO_2$ and/or lactic acid given off by tissues, thereby encouraging tissue metabolism and healing.
N. They can be formed into artificial scabs that are persistant, since polyacrylic acid and its neutralized polymers are non-biodegradable.

O. They do not support bacterial growth since polyacrylic acid or neutralized polymers are non-biodegradable.
P. They resist removal by animals when used in veterinary medicine or surgery.

When in the form of a paste, the invention may be spread on skin or damaged tissues with the fingers or such appliances as spatulas. If applied on a moist surface, a thick layer should preferably be applied to prevent pickup of the rapidly curing gum by adherence to the fingers or other applicator. When in the form of a powdered formulation, it may be applied in a variety of ways, as needed to meet particular requirements, and as would be readily apparent to someone having ordinary skill in this art.

DETAILED DESCRIPTION OF THE INVENTION

This invention makes use of the inventor's discovery that adverse effects of water can be controlled or made beneficial through use of water to activate ionization, acid-base reactions, and related adhesion of compositions to mammalian tissue for hemostasis and/or tissue protection. This discovery hinged on a desire to overcome adverse effects of high humidity that cancelled protection of animals exposed to VX applied onto a hydrophilic coating over skin. It was known that viscosities of aqueous polyacrylic acid dispersions are increased by alkaline neutralization. The seminal idea was that suspension of a dry acidic polymer with a dry alkaline salt in an anhydrous hydrophilic fluid might lead to formation of an adhesive gum after ionization by added water. This idea was initially applied to development of topical skin protectants, then to protective sealing of denuded wounds. The original idea was extended with the thought that artificial clotting of blood might result from ionization of the powdered components by the water in blood or serum. It was found that water, in blood or other leaking body fluids, activates ionization, acid-base reactions and related adhesion of compositions to tissue for hemostasis and/or tissue protection. The basic concept has been extended to encompass at least the six applications (of gum formation induced by water) that are listed in the following outline of applications and usage:

|  | Time frame for use | Removal Method |
|---|---|---|
| Dry powder | | |
| hemostasis | immediate; temporary | debridement, saline, scrub |
| soft tissue splint | soon; temporary | as above, divalent ion sol'n |
| artificial scab | soon or late; prolonged | as above or natural slough |
| Suspension | | |
| topical protectant | prophylactic pre-exposure | divalent ions, NaCl, scrub |
| wound sealant | soon; temporary | as for hemostasis |
| drug vehicle | brief or prolonged | as for wound or from skin |

Each application of the methods of this invention makes use of at least one of two critical classes of components, namely polyacrylic acids or polyvinyl alcohols, in a formulation otimized for the application. However, the polyacrylic acids known as carbomers or carboxypolymethylenes are preferred components. Furthermore, different carbomers are preferred for different applications and usage, as outlined above. Additionally, although non-polymeric components are critical for some applications or usages, ratios of polymeric and non-polymeric components are application specific. The polyacrylic acids may be of various chain lengths and modified monomer components, and have different cross-links as long as they have the monomeric chemical structure $[CH_2=CHCO_2H]_n$, where n is between about 10,000 and about 70,000. The polyvinyl alcohols may also be of various chain lengths and modified monomer components, as long as they have the representative monomeric chemical structure $[CH_2=CHOH]_n$, where n is between about 15,000 and about 150,000.

In particular, any one composition comprises at least one of the following:
(a) a polyacrylic acid having the structural formula $[CH_2=CHCO_2H]_n$, where n is between 10,000 and 70,000,
(b) a composition comprising polyacrylic acid having the structural formula $[CH_2=CHCO_2H]_n$, where n is between 10,000 and 70,000, and desiccated water soluble organic or inorganic base,
(c) a composition comprising polyacrylic acid having the structural formula $[CH_2=CHCO_2H]_n$, where n is between 10,000 and 70,000, and poorly soluble desiccated basic salt, and/or
(d) a polyvinyl alcohol having the structural formula of $[CH_2=CHOH]_n$, where n is between 15,000 and 150,000.

Given the application-specific nature of methods and formulations, particular compositions are described below, both in descriptions of embodiments and in related examples. In particular, formulations for dry storage and applications necessarily differ from compositions with carbomers and non-polymers suspended in water or anhydrous liquid. Therefore, methods of preparation and use may be better understood in connection with descriptions of embodiments and examples. However, some features are held in common, as described below.

Polyacrylic acid (also known as carboxypolymethylene) may be present as a homopolymer in a family of acrylic acid derivatives known as carbomers. Their polyacrylic acid strands may be cross-linked to various degrees with groups such as allyl sucrose. Preferred carbomers have been manufactured under trade names such as CARBOPOL or NOVEON. Such carbomers actively absorb water, melt (without dissolving) at body temperatures, then swell. With water, they constitute a stiff mucilage that is biologically inert but adherent to wet tissue, thereby forming a clot-like wound sealant effective in patients (human or non-human) with hemorrhage from trauma or defective blood clotting (from hemophilia or use of anticoagulant medications such as coumadin).

When the composition includes polyacrylic acid admixed with desiccated water-soluble organic or inorganic base, the acid moiety is neutralized to greater or lesser degree when the composition acquires enough water to support ionic interactions that form salts. Such neutralization, from about pH 4 to pH 8, is known to increase mucilage viscosity in aqueous dispersions. Similar neutralization and induced tackiness is observed when water is added to the dry formulation.

If the composition includes polyacrylic acid admixed with anhydrous basic salts, it is preferable that the salts provide divalent cations, such as $Ca^{++}$ and $Mg^{++}$, that ionically cross-link polymer strands and increase mucilage viscosities to greater degree than monovalent cations, such as $Na^+$ or $K^+$. Physical properties, inertness and low toxicities of such neutralized carbomers are demonstrated by calcium polycarbophil, USP, which is approved by the U.S. Food and Drug administration as a safe and effective over-the-counter bulk laxative and antidiarrheal product. However, calcium polycarbophil USP includes too much calcium ion to serve as an adhesive. With lower concentrations, such divalent cations may ionically cross-link polyacrylic polymer strands while reinforcing the mucilage. Such cross-linking confers properties such as resistance to abrasion and stiffness that are suitable for retention and function as an artificial scab.

Use of calcium hydroxide, calcium carbonate, calcium sulfate, etc. has been associated with stiffness and flexibility with use of magnesium hydroxide, magnesium carbonate, and light magnesium oxide (low density or neoprene grade MgO).

When the composition includes polyvinyl alcohol, one of many commercial products may be used. For example, several of the polyvinyl alcohols known commercially as VINOLS (Air Products and Chemicals, Inc.) and ELVANOLS (DUPONT) have proven useful. As someone having ordinary skill in this art would be aware, polyvinyl alcohol is available in a wide range of degrees of hydrolysis and with corresponding water solubility and other properties. In addition, polyvinyl alcohols can be made more viscous and less water-soluble by a reaction with sodium borate or boric acid or by forming copolymers with carbomers. Such copolymers are of interest, in part, because carbomer molecules act as individual tiny sponges (microgels) when sufficient water is present to separate them. Polyvinyl alcohols, polyvinyl acetates, and polyvinyl alcohols can provide linkages between carbomer microgels. Such linkages may provide film-forming properties not typical of carbomers.

In the methods of the invention, clotting of blood can be facilitated by including in the gel-forming composition at least one calcium salt with a readily metabolized anion (such as gluconate or ascorbate) to provide readily available $Ca^{++}$ to facilitate clotting of blood.

Calcium hydroxide provides enough calcium ions to serve most needs for hemostasis and acid neutralization. However, formulations made with excessive quantities of soluble calcium or magnesium salts lose adhesion to wound surfaces or normal skin. Accordingly, calcium and magnesium salts with limited solubility are preferred. In fact, soluble calcium or magnesium salts can be used to detach a polyacrylic gel from skin or other surface to which it may have been adhered. To minimize the need for excess calcium ions, an anhydrous vasoconstrictive drug, such as L-epinephrine tartrate, may be included in a formulation to restrict the diameters of leaking blood and lymph vessels.

Use of 0.85% physiological saline solution is indicated for gentle removal of formulations from wounds. Sodium ions balance carboxylic sites or displace less abundant divalent ions ($Ca^{++}$, $Mg^{++}$) from neutralized and partially cross-linked polymer sites to create a mucilage that may be removed with copious irrigation and/or wiping. Higher concentrations of divalent ions effectively diminish polymer adhesiveness; their products tend to form doughy lumps that may be readily detached from skin or non-biological surfaces. As indicated in the outline provided above, formulations may be needed either for temporary or prolonged use. Natural healing processes have been observed to remove artificial scabs, much as natural scabs are removed.

The compositions and methods of the subject invention may be widely useful, for instance, in the following applications:

1. Preventing life- or limb- threatening hemorrhage (or minor bleeding) at the site of injury by (a) artificially coagulating blood, (b) adhering the blood/product coagulum over damaged vessels, (c) multiplying the effectiveness of bandages, and/or direct pressure on vessels, to control arterial bleeding, (d) immobilizing damaged tissue to minimize further injury, and, (e) preventing further contamination (and consequent debridement damage) of a wound.

2. Protecting normal or damaged skin, mucous membranes, and wounds from possible injury by coating them with semi-permeable barrier films designed to resist (a) contamination by noxious chemicals, or biological agents, that may occur during warfare, accidents or handling operations, (b) possible damage from decontaminating reagents or antiseptics, and (c) dehydration, maceration, oxygen toxicity and losses of vital fluid constituents through denuded surfaces. For example, powders or suspensions (of compositions of the invention) might be used to stop bleeding from misuse of a razor or to seal and desensitize the raw surface left by a broken skin blister caused by friction or a burn.

3. Maintaining contact with (a) normal skin for deployment of insect repellant, decontaminating reagent, radiation reflectors, sunscreen compounds, camouflage pigments, agent detection indicators, etc., or (b) damaged body surfaces for delivery of therapeutic substances such as vasoactive compounds, antimicrobials, nutrients, or healing promoters.

4. Surgical use to (a) accelerate epithelialization of denuded surfaces, (b) prevent excessive formations of connective tissue during wound healing to avoid scarring, contracture distortions, or keloids, (c) minimize requirements for natural or artificial skin grafts, (d) provide a means for temporary sealing of the bleeding edges of soft internal organs such as liver, spleen, or lung prior to the application of biodegradable materials by highly skilled surgeons, and (e) stop bleeding within body orifices (e.g., nosebleed, uterine hemorrhage, and bleeding from injuries or surgery such as dental extraction or tonsillectomy).

5. Use as a bioadhesive to stabilize damaged tissue (as a soft tissue splint), coat and seal raw surfaces (such as blister bases, abrasions or burns), and protect ulcers (or similar lesions) to facilitate use of compression bandaging. Such applications are not to be confused with known uses of carbomers for cosmetic products, attachment of prostheses, retention of dentures, usage in buccal adhesives, or in tablets for adhesion to buccal surfaces.

6. Use as a vehicle for delivery of drugs to or through wounded surfaces, skin lesions, mucous membranes, or normal skin. Such drugs might include (but are not limited to) substances used to promote healing (antimicrobials, osmotic colloids, proteolytic enzymes, growth factors, steroidal or non-steroidal anti-inflammatory drugs, nutrients, etc.).

Some novel features of this invention include: (a) significant protection from exposures to a wide variety of biological or chemical warfare, (b) opportunity for manipulation of the properties of an acrylic acid/alkaline salt hydrated product by varying the content of salts (for example, it has been found that mixtures with high content of sodium salts tend to form artificial clots that are soft and pliable, whereas calcium salts tent to impart rigidity and magnesium salts tend to impart rubbery tendencies), and (c) sealing of shallow wound cavities with suitable mixtures of calcium, magnesium and/or sodium salts. It was observed that such action was followed by production of adherent artificial scabs under which epithelial cells were protected and able to bridge larger cavities than would otherwise be epithelialized. Accordingly, such artificial scabs appear to offer protection from undesirable development of scar tissue and subsequent disfiguring contractures and/or an increased risk of cancerous tumor formation.

This invention is designed to convert what are commonly thought to be disadvantages (of wetness in a wound or on a skin surface) into advantages. Existing alternatives usually address the problem of unwanted water by using one of two approaches. One is use of materials as barriers or as absorbers of water. Examples include use of bandaging fabrics, water-resistant polymers, skin grafts, and hydrophobic compositions, such as petroleum jelly. In many cases they are used to retain blood clotting components until clotting accomplishes in situ blockage more slowly than artificial clotting produced by the presently described invention. An alternative approach is to interrupt the supply of blood/water. Examples of this approach include clamping of vessels with hemostats, use of cautery, and coagulation of tissue proteins with acids.

High efficiency is based on low costs, weights and bulk volumes needed for the anhydrous materials, and their rapid deployment potential. The ease of applying free-flowing powders is insured because thickening or melting occurs subsequently, in situ. Primary components are compatible with wet surfaces for adhesion, surface sealing and delivery of anhydrous antibiotics or other medicaments.

To minimize post-injury trauma to damaged tissues, hemostatic powder could be sprinkled on one or both of two opposing surfaces before they are brought together. Water from the facing surfaces induces adhesion to "glue" the surfaces together. Bandaging and stiffening materials could be adhered to damaged tissues in the same manner. In either case, the injured tissues could be stabilized to prevent additional damages. This soft tissue splinting could serve the same purpose as splinting of fractured bones: to minimize subsequent damage. To promote healing, applications to wounds can be built up to stabilize ragged edges and maintain an osmotic balance such that the damaged tissues can be maintained with minimal drying out or displacement during transport of a patient to a surgical facility. For skin defense coatings, compatibility with wet surfaces means that products can be applied on perspiring skin or during rainfall, to deliver detoxifying reagents onto contaminated skin or to provide prophylaxis against contact with chemical warfare agents.

Adhesion is activated at the source of bleeding or fluid loss. Since direct sealing action proceeds outward from the damaged site, this sealing orientation provides maximal efficiency in blocking vessels, or coating denuded surfaces and normal skin. Also, this orientation permits observation of any arterial blood breakthroughs so that, if necessary, pressure occlusion can be maintained during the brief time period (usually less than 1 minute) that is required for completion of the acid-base reaction or melting enough to provide contact with surfaces and effective reinforcement of the seal. However, time for maximal adhesion is related to the amount of blood/water already present and to the volume and distribution of the powder to be wetted. Larger boluses of hemostatic powder and increased diffusion time are needed as volumes and flow rates of blood increase.

This invention includes compositions and methods for use of unadorned polymers as the most simple embodiment of the novel concept that a biocompatible polymeric powder can combine with the water of blood to create an artificial clot in situ. In fact, polyacrylic acid powders need not be neutralized to satisfy some uses described for multi-component formulations. This approach has the inherent advantage that some polymers are generally recognized as safe (GRAS) for contact with human tissue. To this end, it is noted that polyacrylic acids are frequently and safely used in dentistry. However, demonstrations of safety and efficacy are generally required for new uses or mixtures of GRAS substances. This fact indicates that safety testing may be required for each proposed composition and for use of unadorned polyacrylic acid powders on wounded tissue.

A preferred operation of this invention involves formulation of a finely divided anhydrous mixture including a polymeric acid and at least one non-corrosive alkaline calcium salt, so that the packaged, unreacted components can be applied onto a bleeding wound or other body surface. Such action leads to ionization or melting of the polyacrylic acid to form an adhesive gel or gum that tenaciously adheres to damaged tissues for service as an artificial blood clot or barrier layer. The addition of water to dry polyacrylic acid lowers the glass transition temperature from above 115 degrees centigrade to well below mammalian body temperatures. It is this melted product (water plasticized) that adheres to wet tissues.

Experience with carbomers available during the conflict in Viet Nam (such as a family of crosslinked poly(acrylic acid) products produced by Noveon, Inc., under CAS # 9003-01-4 and referred to as Carbomers 934, 940 and 941) and a recently available product (Carbomer 974P NF, also produced by Noveon, Inc., under CAS # 9003-01-4) suggests that an another product (Carbomer 971P NF, also produced by Noveon, Inc., under CAS # 9003-01-4) has a more desirable balance of reported properties and may be the preferred carbomer for hemostatic purposes. The ratios of carbomer to calcium salt may vary over a wide range. For instance, hemostasis has been successfully demonstrated when the composition comprised 100% carbomer and no calcium salt, and when the composition comprised up to 50% (w/w) of Carbomer 974P NP, also produced by Noveon, Inc., under CAS # 9003-01-4) and 50% of calcium polycarbophil (sold as NOVEON CA-2). As explained more completely below (in an example) mixtures with more than 50% NOVEON CA-2 do not adhere well to tissue. Utility of calcium ions is expected to be greatest where a composition is in contact with unclotted blood, to assist fibrin-based clotting. Accordingly, incorporation of a soluble calcium salt into a carbomer copolymer film has been projected as a method for (a) delivery of differing calcium ion concentrations for wound interface and gel forming strata, and (b) packaging of hemostatic powder boluses for precise placement and application of indirect pressure.

Properties that promote hemostasis are pre-eminent if fatal hemorrhage is possible but protection of tissue may be pre-eminent in other circumstances. For tissue protection, the preferred ratio of polymer to calcium ion donor ratio will be as needed to yield a gel pH of about 7.4 at the gel/tissue interface. The preferred calcium ion donor formulation will be as needed to approximate osmolarity of 0.85% sodium chloride solution. For tissue protection alone, the preferred non-polymeric formulation will provide a physiological balance of sodium, potassium, calcium and magnesium ions at the gel/tissue interface, in the presence of the particular carbomer or copolymer, during the expected period of gel/tissue contact.

It is noted that there is one prior composition that yields a familiar substance by means of a process somewhat similar to that of the described invention. That composition also involves the formulation of powdered material, use of water to activate adhesion of the primary material to particulate and fibrous substrates, and retention of the ensuing mixture in situ until curing takes place. Similarly, that substance is used to block the unwanted flow of watery fluids and to create water-resistant coatings. However, that prior substance operates by trapping water in hydrated form. Furthermore, it cures slowly and is far too alkaline and inflexible for biocompatibility. That substance is known as portland cement.

Various uses and applications of the described methods are discussed below in greater detail. Obviously, this is not an exhaustive list of all uses of the invention, as would be apparent to someone having ordinary skill in this art.

1. Hemostasis

In a preferred embodiment, this invention consists of a method for artifically clotting blood or body fluids by employing their water content to change anhydrous polymeric particles into a gel that adheres to wet tissue sufficiently to block flow from blood vessels or damaged surfaces. This method can be implemented with any one of the carbomers (or their copolymers) and carbomer compositions as described above, if the powdered composition is (a) applied to the tissue in quantity sufficent to absorb all watery exudate (blood or fluids), and (b) held firmly in place until normal clotting has sealed bleeding vessels, or adhesion to tissue is sufficient to block flow from embedded arteries.

The effective carbomers consist of (1) various forms of polyacrylic acid and/or other biocompatible polymers (such as polyvinyl alcohol, polyvinyl acetate, or polyvinyl pyrrolidone). In a most preferred embodiment, the compositions include anhydrous alkaline substances that neutralize the various forms of polyacrylic acid, or copolymers, to (a) increase the viscosities of the gels, and/or (b) modify formulations to serve intended surgical uses. These uses include hemostasis, wound sealing to retain body substances, formation of protective coatings to exclude injurious substances, and/or fostering of healing and epithelialization. One known role of alkaline components in the art of polyacrylic acid use is the neutralization of acidic sites of polymer chains. Such neutralization is often used to substantially increase gel viscosity and adhesive strength of compositions largely composed of water. In the described method, water is excluded from compositions until it is available from blood or tissue fluids. In this embodiment, dry divalent alkaline salts of calcium and/or magnesium are mixed with dry polymers using equpment used in the art to prepare dry compositions before packaging. Dry divalent salts add to gel viscosity (when moistened), apparently by forming ionic links between adjacent polymer filaments, and with negatively-charged sites of tissue biopolymers, such as proteins and peptides when the divalent cations are mobilized by water to interact with anionic carboxylic sites of polyacrylic acid polymers.

For instance, the polyacrylic acid known commercially as Carbomer 941 (a crosslinked poly(acrylic acid) products produced by Noveon, Inc., under CAS # 9003-01-4) (and related acidic polymers) reacts rapidly in the presence of water to form gels with sodium salts or poorly soluble gums with calcium or magnesium salts. Anhydrous sodium borate elevates pH, absorbs water of hydration and, in the presence of water, reacts with polyvinyl alcohol to form a poorly soluble gel. In the presence of water, polymeric or polymeric and non-polymeric components become organized as a hydrophilic gel that adheres to damaged tissues while entrapping lost cells, proteins and salts. Such gels adhere without the clotting time delay observed with blood components. Some of the gels may present as films. Other gels may evolve into artificial scabs that are semi-permeable to water, oxygen, and carbon dioxide.

The method of the invention may include the further step of applying pressure to the site of the wound/denuded area/burn, which would be effective to collapse blood vessels and restrict further hemorrhage while sufficient water is absorbed by the composition to form a gel and staunch blood flow. The duration of this step will vary with the size of hemorrhaging vessels, sufficiency and amount of the composition, and avoidance of excessive shearing movement, but is expected to begin immediately after application of the composition and may be completed within about one to five minutes. If the powder is not distributed effectively at first, the operator may need to move it around until all powder is wetted. If insufficient powder has been applied initially, more can be applied over any wet spot until hemostasis is complete. If it is appropriate to reinforce or extend the perimeter of an existing gel, more powder and/or more water may be added. However, water should be applied gradually to avoid softening of the existing gel.

In a preferred embodiment of this invention, the powdered composition is retained behind a membrane or enclosed within a bag of polyacrylic acid film or carbomer-copolymer film, with or without incorporated calcium ions to aid fibrin-based clotting of blood. The sequestered composition is further enclosed within a sterile heat-sealed envelope designed to be readily opened (with a tear strip or similar device) so the polymer film is presented on one side of the envelope residue. The back of the envelope is used to separate an operator's fingers from the film and/or the composition. The operator would be expected to place the film against the wound to displace pooled blood and apply indirect finger pressure (about 5-10 pounds/square inch) over any apparently transected blood vessel(s). The film disintegrates, in contact with water of blood or damaged tissue, to permit wetting of the released bolus of powder for adherence to wounded tissue.

In an alternate method, the loaded sponge is folded within the envelope to retain the powdered composition. This arrangement permits the user to release the fold and apply the composition onto the target site. The sponge and envelope may be held in place then left to serve as an external reinforcement of the gel. After a gel is formed, the sponge and envelope might be wrapped with suitable pressure bandaging to avoid displacement. However, a volume of composition at least equal to the volume of a deep wound may be required. In such cases, the envelope may be removed so that additional loaded sponges may be deployed over or adjacent to the first one. In general, the compositions might be applied in large volume (as desired) directly into a life-threatening wound from a large package, dispensed from a puffer tube onto an oozing, burned or abraded surface, or a small loaded pad might be applied directly over a superficial wound (as with an adhesive bandage). Likewise, compositions might be sifted from a shaker type container, or blown out of a pressurized container, etc. Although some packaging might be designed to satisfy military requirements, non-military users of this invention might employ a wide variety of packaging available to those skilled in the art. However, packaging must store the composition in desiccated form for rapid delivery at a wound or body surface. Once the composition has been applied to the targeted site, additional water may be added (slowly) to the outside surface of the composition to provide a durable anti-hemorrhagic plug of a wound or to improve the thickness and protective capacity of a wound sealant after blood flow and water diffusion has been stopped.

One of the most important uses of the described formulations would be as a readily carried sterile powder within sterile packaging designed to permit immediate control of hemorrhage under field conditions. Typical components might be packaged inexpensively within readily deployable heat-sealed envelopes or pouches. The contents of these packages would be added and sealed up under sterile conditions. Any inorganic components (such as calcium hydroxide) could be readily sterilized with dry heat. However, dry carbomers tend to fuse above 110 degrees Centigrade. Although the products are sterile when freshly synthesized, processing machinery has not been designed to assure continued sterility. Therefore, the manufacturer does not currently warrant any products as sterile but does agree to replace any products found to contain viable organisms. Since the dry products can be held for many hours at 100 degrees Centigrade, it appears that sterile products could be kept sterile by processing and packaging at that temperature.

2. Soft Tissue Splint

Another embodiment of the invention entails a skin and soft tissue adhesive composition comprising at least one of the above-described gel-forming compositions. If bleeding is considered to need correction, a preferred composition might be identical to that of a dry powder optimized to control hemostasis. If the primary consideration is to stabilize and protect tissue (as during an expected long stay in an ambulance), the preferred non-polymeric components would be different. For tissue protection, the preferred non-polymeric formulation will provide a physiological balance of sodium, potassium, calcium and magnesium ions at the gel/tissue interface, in the presence of the particular carbomer or copolymer, during the expected period of gel/tissue contact. The preferred polymer/non-polymeric ion donor ratio will be as needed to yield a gel pH of about 7.4 and approximate osmolarity of 0.85% sodium chloride solution at the gel/tissue interface. For this embodiment, the non-polymeric components may include antimicrobials as indicated in surgical art. When a preferred composition contacts water, the gel-forming compositions react with the water to form an adhesive gel that adheres to skin and soft tissue. Use of a hemostatic powder to 'glue' surfaces of a wound together might be indicated to support and stabilize (splint) damaged soft tissues. Later, the surgeon working on the injured individual will likely want to remove the composition in the operating room. Thus, in that case, the constituted adhesive gel would serve as a temporary expedient and soft tissue splint. Optionally, as indicated by military requirements, the composition may include one or more of an antibiotic, blood-clotting enzymes, decontaminating reagents, detoxifiers, pH indicators, vasoconstrictive agents, or compositions capable of indicating the presence of toxic or infectious compounds.

In a further embodiment of the method, the dry components of a tissue glue/soft tissue splint might be formulated with deionized water to form a paste or mucilage. Such a formulation might be used as a soft tissue splint if hemorrhage or fluid loss has been controlled. Such a formulation may have the same dry components, in the same relative proportions, as needed to protect tissues with a dry soft tissue splint composition. Such a formulation could be made by applying the existing art for formulation of moderately viscous consumer products such as dental adhesives. Such pre-formed gels may be packaged in collapsible tubes of various designs, as known in the art. Accordingly, such sterile compositions may be extruded or expelled directly onto denuded surfaces. They might be spread through apposition of damaged tissues by gentle manipulation of adjacent undamaged surfaces or by use of sterile sponges, instruments, or gloved hands.

However, very little added water would be needed to separate the swollen microgels and induce separation of the tissues that might be glued together with an undiluted paste. On the other hand, powdered carbomer formulations do not provide adhesion in the absence of sufficient water to establish an adherent gel. If spacing and cushioning of damaged tissue is needed, rather than firm adhesion, a formulation of carbomer with physiologically balanced electrolyte ions can be made with enough light magnesium oxide to make a rubbery product with low adhesion. Accordingly, some care will be needed for selection of preferred compositions for use as soft tissue splints or temporary tissue glues in specific cases.

As an additional embodiment of tissue glues, either dry or as pre-formed gels, adherence of carbomers to skin might be exploited for temporary attachment of small objects to skin. For example, electrocardographic electrodes might be attached to the chest to permit recording during strenuous exercise. For this purpose, a preferred formulation would employ one of the carbomers known in the art as electrolyte resistant. A patch could be constructed with a high electrolyte concentration in a core in contact with a metal lead and an electrolyte-free perimeter arranged to assure firm attachment to moistened skin. A carbomer with balanced electrolytes might serve to attach costume jewelry to moistened ear lobes.

3. Artificial Scab to Promote Healing

In an additional embodiment, formulations of the above-described compositions can be used to protect denuded tissue from further damage. Such damage might ensue from losses of body substances (such as water, blood, plasma, serum, proteins, electrolytes, nutrients), and from access of and further damage by normal environmental substances (such as oxygen, dirt, foreign protein antigens, pathogens, saprophytes, etc.). Preferred compositions for this embodiment will provide tissue protection, and accordingly they will be formulated with physiologically balanced electrolyte ions to make a gel providing physiologic osmotic and pH properties. Such compositions are preferably formulated with enough light magnesium oxide to make a slightly rubbery product but the MgO/polymer ratio will be low enough to assure firm adhesion to damaged tissue. The preferred use of such compositions will be application as a dry sterile powder sifted or dropped directly onto wounded or burned surfaces. Such surfaces should be free of obvious or likely contamination but losing blood or tissues fluids rapidly enough to establish a gel within about ten minutes or less. In such cases, sufficient powder should be applied (or re-applied) to assure an initial gel thickness of about two to five mm. As an alternative, the dry components might be formulated with deionized water to form a paste or mucilage, as described for soft tissue splinting or use as a tissue glue. The art for packaging and deployment of described pre-formed gels might be used to generate artificial scabs on denuded surfaces exhibiting sparse loss of blood or fluids.

A variety of formulations, used primarily for hemostatic and wound sealant applications, have been observed to function as artificial scabs. Artificial scab observation with some of these formulations are described in the Examples section, below. Formulations designed to provide tissue protection, as described above for use as tissue glues or in soft tissue splinting, represent preferred compositions for artificial scab formation. If used as dry powders, they would be sifted into a wound with intent to generate a gel of thickness between about two and about five mm thick. If the wound does not provide enough water to generate a gel at least two millimeters thick, sterile water might be added drop-wise to wet the wound before and/or after application of the powdered composition. A pre-formed aqueous gel should be spread on a denuded surface to a depth of about five to ten millimeters.

A further embodiment is suggested by observations made during actual military conflict. Formulations later observed to form artificial scabs were applied to wounds of rabbits made by completely removing full thickness skin as a disc about three centimeters wide. This was done with anesthetized rabbits to test protection against contamination with chemical warfare agent CS, then in uses in military combat situations. Accordingly, control wounds were exposed to CS without such protection. The control wounds developed normal scabs and their skin perimeters rapidly contracted to substantially reduce areas of exposed muscle. This is a normal and desirable response of loose skin, as found on rabbits and cats. Perimeters of similar human wounds do not contract significantly. Instead, they tend to fill with connective tissue which later contracts to form scar tissue. In rabbits which formed artificial scabs, the scabs largely prevented normal constriction of skin. Subsequently it was later observed that the combination of natural and artificial scab formation allowed the rabbits to re-epithelialize much of the denuded surface under the artificial scab. Thus, establishment of artificial scabs over denuded human wounds would reasonably be expected to similarly accelerate re-epithelialization and correpondingly reduce scar tissue formation.

If left undisturbed in contact with the denuded surface, a preferred composition (a carbomer, balanced electrolytes, light MgO, pH near 7.4, osmolarity like physiological saline, antimicrobial content) might provide a protective shield to limit development of fibroblastic tissue and support epithelialization. This shield could serve as an artificial scab to protect the wounded area from losses of body substances and further damage, as caused by environmental substances or solar radiation, that often leads to formation of disfiguring scar tissue. This method might be used, with application of a preferred composition in dry form or pre-formed aqueous gel, to promote migration of epithelial cells over underlying tissue. Such use might be expected to re-establish epidermis more rapidly, and over a larger area, than would otherwise occur. Additionally, an open wound or denuded or burned body surface may be protected from environmental access and further damage by chemical warfare agents, biological warfare agents, noxious industrial substances, and/or other toxic substances that may constitute hazards to unprotected wounds or tissues.

Further, the open wound, denuded body surface or burned skin may be exposed to therapeutic substances incorporated as desiccated soluble drugs that would become dissolved in water from the tissue and gel. They would diffuse preferentially into the tissues from the mucilage. These drugs might include (but would not be limited to) antibiotics and sulfonamides, or trauma reduction agents such as antioxidants and nutrients. For instance, growth factors or cytokines useful for keeping cells alive and proliferating might be included. These could healing under a protective covering of polymeric gel and incorporated blood product residues.

4. Topical Protectant

In another embodiment, the invention-contemplates methods for reducing skin exposure and penetration by chemical warfare agents, as described above. This method comprises the step of coating skin with a composition comprising (a) at least one of the compositions selected from the group consisting of (i) a polyacrylic acid having the structural formula $[CH_2=CHCO_2H]_n$, where n is between 10,000 and 70,000, (ii) a composition comprising polyacrylic acid having the structural formula $[CH_2=CHCO_2H]_n$, where n is between 10,000 and 70,000, and a desiccated water soluble organic or inorganic base, (iii) a composition comprising polyacrylic acid having the structural formula $[CH_2=CHCO_2H]_n$, where n is between 10,000 and 70,000, and a desiccated poorly soluble basic salt, and (iv) a polyvinyl alcohol having the structural formula of $[CH_2=CHOH]_n$, where n is between 15,000 and 150,000, (b) at least one anhydrous hydrophilic liquid, capable of resisting penetration of chemical warfare agents or other noxious compounds, in which the polyacrylic acid and the alkaline salt are suspended and which permits the polyacrylic acid to form a gel in the presence of water. Such an anhydrous hydrophilic fluid would be selected from among those found to resist diffusion by various lipophilic chemical warfare agents. Such fluids include (but are not limited to) nitrile silicone fluid, polyoxyalkylene glycols, and anhydrous liquid surfactants; and (c) optionally, one or more of decontaminating reagents, detoxifiers, camouflage pigment, pH indicators, agents capable of detecting the presence of toxic or infectious compounds, sodium borate, calcium hydroxide, calcium gluconate, magnesium oxide, etc. As a topical skin protectant to defend against agent contamination, the composition acts a hydrophilic defense in depth. It might be expected to provide protection that varies with protectant coating thickness, in general, and the specific agent, in particular.

When the composition comprises one of (i), (ii) or (iii) of component (a), the composition may further include an anhydrous hydrophilic media or liquid, in which the polyacrylic acid and the alkaline salt are suspended and which permits the polyacrylic acid to form a gel in the presence of water. Specific compositions prepared for testing as topical skin protectants and results of their use.

5. Wound Sealant

In another embodiment, the invention involve a method for wound protection that relates to a family of compositions (and the use thereof) that contain at least one of the above-described compositions, which further contains an alkaline salt that may be used as a dry powder or be suspended in an anhydrous hydrophilic media, or in an aqueous gel. Accordingly, the compositions and methods described for embodiment in artificial scabs could serve in this embodiment. The polyacrylic acid known commercially as Carbopol 941 (a crosslinked poly(acrvlic acid) products produced by Noveon, Inc., under CAS # 9003-01-4) (and related acidic polymers) will react rapidly in the presence of water to form gels with sodium salts, or poorly soluble gums with calcium or magnesium salts. For brief use to protect wounded personnel from exposure to chemical warfare agents, the dry reactants might be suspended in poorly-soluble hydrophilic liquid media, such as a polyoxyalkyene glycol or nitrile silicone fluid. Such fluids were identified in screening tests designed to detect resistance to transit by chemical warfare agents. Accordingly, such compositions are useful to protect skin from penetration by harmful substances or organisms and may be useful to protect damaged tissues and to regulate water loss. Thus, the compositions could both "stick" to wounded tissue and extend over neighboring skin to seal off a wound. Examples of formulations that protected animals and human skin from irritant or vesicating effects of CS-2, and animals from the lethal effects of 4 $LD_{50}$ doses of VX, are given below.

It has been found that gel properties are affected by the choice or proportions of different cations and by physical sizes and shapes of dry components. Formulations for use as wound sealants may include antimicrobials, vascular constrictor or anti-inflammatory drugs, pH indicators or systems, chemical agent indicators/detoxifiers, sunscreens, camouflage pigments, or other components added to support particular military applications. Antibiotics or other medicaments can be incorporated into modified formulations intended for wound or burn dressing to provide intimate, continuous contact with the damaged tissue. The suspensions could be applied readily as creams or pastes but they would absorb ambient and tissue water to cure in situ as tough films. Packaging and handling of polymeric and non-polymeric components in suspensions made with non-aqueous liquids may be expected to resemble methods described with regard to aqueous gels for embodiment as tissue glue/soft tissue splints or in artificial scabs.

6. Drug Vehicle.

Another embodiment concerns use of the methods and compositions described for wound protection in a different role as drug delivery vehicles. The same dry or pre-formed gel compositions might be used primarily to deliver antimicrobials or a variety of other drugs into a wound or other surface of a patient. In particular, it is anticipated that drugs currently given systemically (to achieve useful concentrations in wounded tissues or diseased surfaces) could be delivered locally from the described hydrophilic gels. In this manner, higher local drug concentrations and lower blood concentrations could be achieved, if only local effects are needed. As mentioned above, such local use of hydrophilic gels might be expected to promote transfer of hydrophobic drugs into hydrophobic skin and tissue membranes.

7. Kits

In a different embodiment, the invention contemplates various kits that can be used in conjunction with any of the above-mentioned embodiments, and other embodiments not described in so much detail. Other kits may be used for hemostasis, soft tissue splinting, artificial scabs, topical protectants, wound sealants and as drug delivery vehicles. The kits must have, as a minimum and packaged in association, one of the above-described compositions and either a dispenser for applying the composition as desired or instructions as to how to properly use and apply the composition. The dispenser may be, for instance, a non-woven fabric, a woven fabric, a tube, a bandage impregnated with the composition, or a container having an opening through which the composition may be dispensed.

For instance, one kit may be designed for reducing blood or fluid loss from open wounds, denuded tissue or burned skin in a mammal. The kit comprises, packaged in association, (i) a gel-forming composition comprising at least one of the above-described compositions, which upon application of the composition to the site of the open wounds, denuded tissue or burned skin, reacts with water present in blood or other bodily fluid exposed in the site to form a gel that adheres to the site and reduces loss of blood or bodily fluid, and (ii) a dispenser for applying the composition to open wounds, denuded tissue or burned skin.

Another kit is useful for reducing skin exposure and penetration by chemical agents that could include GB, GD, VX, HD, CS-2, CN and EA3580. It comprises, packaged in association, (i) a gel-forming composition comprising at least one of the above-described compositions; and (ii) a dispenser for applying the composition to skin.

In all of the kits, as appropriate, optional components may include one or more of an antibiotic, blot-clotting enzymes, decontaminating reagents, detoxifiers, camouflage pigment, pH indicators, vasoconstrictive agents, agents capable of detecting the presence of toxic or infectious compounds, starch, sodium borate, calcium hydroxide, calcium gluconate, magnesium oxide and borax. The anhydrous hydrophilic liquid is preferably one of polyoxyalkylene glycols, nitrile silicone oils, or certain anhydrous surfactant liquids.

EXAMPLES

The detailed description of this invention is made more complete by specific examples, which are best understood in their developmental context. The topical skin protectant known as M-5 ointment was the only composition issued by the U.S. Army during World War II for skin defense against chemical agents. It was effective against HD but ineffective or detrimental with other agents. Its lipophilic base tended to increase agent penetration of skin by trapping water in the barrier layer of the epidermis. An oxidizer in M-5 ointment converted one of the nerve agents into a severe skin irritant. Therefore, M-5 ointment was withdrawn from issue.

During the era of the conflict in Viet Nam, there was no topical skin protectant known to shield soldiers from toxic chemical warfare agents that penetrate skin. A need for protection of perspiring, hydrated skin was identified. A hydrophilic polyethylene glycol (CARBOWAX 1500, of Union Carbide and Chemical Corp., and designates a water soluble linear poly(oxvethylene) having CAS # 2532-68-3) was used as a control standard to protect rabbits from chemical warfare agents applied in the laboratory. However, this water-soluble skin coating failed to protect in humid air. Therefore, screening was performed to identify water-resistant hydrophilic substances. Those identified were anhydrous syrupy liquids. Thereafter and to the present, thickeners reactive with water were sought to accomplish increased protectant viscosity in a humid atmosphere. Prototype formulations and skin protection results are described in example 1.

Example 1

Formulation A 3 gm starch, 2 gm sodium carbonate, 4 gm sodium bicarbonate, 21 gm CARBOWAX 1500 (Union Carbide Corp. brand of polyethylene glycol, a water soluble linear poly (oxyethvlene) having CAS # 2532-68-3)

Formulation B 1 gm polyvinyl alcohol, 2 gm dehydrated sodium borate, 3 gm CARBO WAX 1500 (see above for description).

Formulation C

15 Gm CARBOPOL 941 (see above for description), (B.F. Goodrich brand of carboxypolymethylene), 7 gm dibasic sodium phosphate (anhydrous $Na_2HPO_4$), 8 gm light magnesium oxide, 70 gm UCON LB 1715 (Union Carbide Corp. brand of polyoxyalkylene glycol, a poly(propylene oxide) monobutyl ether having CAS # 9003-13-8)

Formulation D

80 Gm PLURONIC P65 (anhydrous surfactant liquid, known generically as polaxamers and chemically as poly (ethylene oxide)-poly(propylene oxide) block co-polymers, having CAS # 8061-52-7), 10 gm borax, 5 gm sodium carbonate, 5 gm Vinol 205 (partially hydrolyzed polyvinyl alcohol)

Formulation E 90 gm P65 PLURONIC (see above for description), 2.6 gm CARBOPOL 941 (see above for description), 1.3 gm light magnesium oxide Formulation F 90 gm P65 PLURONIC (see above for description), 5 gm CARBOPOL 941 (see above for description), 5 gm calcium oxide.

Depilated rabbits were coated with the described formulations, which were challenged with a standardized exposure dose of CS-2 (CS riot control agent treated to facilitate aerosolization). The combination of alkaline salts in formulation A was selected to produce a product of about pH 9, to be safe for skin yet facilitate rapid alkaline hydrolysis of the limited amount of certain lipophilic skin penetrants that can dissolve in a hygroscopic polyglycol derivative. Starch and various other polysaccharides absorb water and act as stabilizers of the very soluble polyglycols. Anhydrous sodium borate in Formulation B elevates pH, absorbs water of hydration and, in the presence of water, reacts with polyvinyl alcohol to form a poorly soluble gel. CARBOPOL 941 (Carbomer 941, see above for description).) of formulation C is one of several carbomers that, in the presence of water, react rapidly to form gels with sodium salts, or poorly-soluble gums with magnesium salts. UCON LB-1715 (see above for description), is a syrupy anhydrous liquid found to resist diffusion of lipophilic substances, apparently because it is hydrophilic although it is not very soluble in water. The ingredients were readily worked with a spatula to yield pastes with readily soluble CARBOWAX 1500 (see above for description), or less soluble hydrophilic media such as P65 PLURONIC (see above for description) or UCON LB-1715 (see above for description). Each of these formulations was found to visibly reduce skin redness and latent blistering (Nikolsky's effect) produced by CS-2 on control skin. It was concluded that, in some cases, protection was the result of alkaline hydrolysis of the agent. This effect was indicated by the accumulation of yellow CS breakdown products on protective coatings. In other cases, the low solubility of CS, VX (and other skin penetrants) in hydrophilic media appeared to convey protection against agent diffusion by reducing diffusion rates across the barrier layer.

Example 2

Additional formulations were prepared to explore effects of differing inorganic salts, usually with polymer and liquid vehicle content held constant:

Formulation G 3 gm light magnesium oxide, 3 gm CARBOPOL 941 (see above for description), 14 gm UCON LB-1715 (Union Carbide Corp. brand of polyoxyalkyene glycol) (see above for description).

Formulation H 3 gm magnesium hydroxide, 3 gm CARBOPOL 941 (see above for description), 14 gm UCON LB-1715 (see above for description), Formulation I 3 gm magnesium carbonate, 3 gm CARBOPOL 941 (see above for description), 14 gm UCON LB-1715 (see above for description)

Formulation J 2 gm magnesium carbonate, 1 gm sodium carbonate, 3 gm CARBOPOL 941 (see above for description), 14 gm UCON LB-1715 (see above for description)

Formulation K 1 gm light magnesium oxide, 2 gm sodium carbonate, 3 gm CARBOPOL 941 (see above for description), 14 gm UCON LB-1715 (see above for description)

Formulation L 3 gm light magnesium oxide, 3 gm anhydrous dibasic sodium phosphate, 6 CARBOPOL 941 (see above for description), 28 gm UCON LB-1715 (see above for description).

Each of these formulations was applied on clipped rabbits and challenged with CS-2. It was observed that relatively alkaline formulations (H and J) showed yellow-orange coatings of CS degradation products but a less alkaline formulation (L) did not. However, each formulation demonstrated complete protection of the rabbits from effects of CS exposures seen in controls. Therefore it was concluded that formulations adjusted to physiological pH (7.4) would have potential both as wound protectants and as vehicles to deliver sulfonamides or antibiotics into wounded or burned tissues.

Example 3

Sets of three rabbits were coated, respectively with formulations G, J or L, then challenged with 4 times the 50% lethal percutaneous bare skin dose of nerve agent VX marked with a fluorescent tracer, Hiltamine Arctic White. All of the rabbits were in good condition after 24 hours of exposure. Ultraviolet light revealed spread of Hiltamine to make a spot about 7 mm in diameter. About half of the rabbits had local twitching of skin at the application site, but no other signs were observed. This test showed that Formulation L yielded a tough film of about pH 8.5 after application on dry skin, where it was cured in place by ambient moisture or insensible water loss from bare rabbit skin. Formulation L prevented VX penetration that would have caused local skin twitching. This testing showed that the described formulations are effective against the primary percutaneous nerve agent threat to soldiers and that such formulations maybe useful for retention of an agent-resistant coating on wet skin.

Example 4

Since rabbits do not perspire, a number of materials considered useful to defend rabbits against CS skin exposures were placed on separate areas of both arms of an investigator. The investigator was exposed to simulated Southeast Asia conditions of temperature and humidity and was observed to perspire. Four formulations were worn under occlusive patches adhered to tender skin of the forearm. No skin irritation was observed after 32 hours of wearing formulations G, H, J and K under occlusive patches. Formulation G yielded a complete, slightly brittle plaque. Formulation I tended to bunch up and was slightly brittle. Formulation J yielded a complete, slightly brittle plaque. Formulation K yielded a complete but sticky and tough plaque. These results indicate that differences in product composition can be engineered without undue experimentation to provide an agent-resistant coating that also resists perspiration of human skin.

Example 5

During the Viet Nam conflict some soldiers were obliged to search abandoned Viet Cong tunnels after riot control agent CS-2 had been introduced into the tunnels to flush out the enemy. Skin exposures to CS-2 had been shown capable of inducing large blisters. There was concern that CS-2 would cause unusual problems if it became a wound contaminant. An outcome of this concern was a very small program for development of a "wound sealant" to exclude CS-2 and the many other contaminants found in Viet Nam. Rabbits were placed under long-acting anesthesia and wounded in various ways to test the need for protection against CS-2. Initially, wounds were created by snipping discs of skin and underlying muscle out of clipped backs. CS-2 was sifted into control wounds, and over wounds coated with applications of wound sealant suspensions or their dry powdered components. Applied suspensions (represented by Formulations C, D, E and F) or dry powders (similar ratios of dry components without an anhydrous liquid) were rapidly changed into artificial scabs that adhered to the wet tissues. Although a yellow decomposition product formed on some of the artificial scabs, there were no signs of acute damage from CS-2 in unprotected wounds. However, it was noticed that wound healing occurred more rapidly under artificial scabs than in their absence. Furthermore, it was observed that normal contraction of wound edges was clearly inhibited by mechanical resistance of the artificial scabs. It was concluded that the tested formulations not only provide protection of wound from chemical warfare agents but also facilitate skin healing and minimize potential for scar formation.

Example 6

The first dry mixture applied to freely bleeding rabbit wounds consisted of a formulation called #312G. This consisted of 4 gm Carbopol 934 (a crosslinked poly(acrvlic acid) product produced by Noveon, Inc., under CAS # 9003-01-4), 2 gm $Ca(OH)_2$, 1 gm calcium gluconate, and 0.08 Gm L-epinephrine bitartrate. About half of a teaspoonful (about 8 mm$^3$) of #312E powder was loaded onto a 2×2-inch cotton gauze surgical sponge. A post-experimental rabbit was anesthetized. Scissors were used to cut though the marginal ear vein of one ear. The loaded sponge was clamped around the cut with finger pressure and held for about 15 seconds before pressure was released. It was then noted that bleeding had been stopped completely. Subsequently the abdomen was opened to expose the liver for excision of a piece about three-fourths of an inch wide. Bleeding from the oozing surface was promptly stopped by dusting it with the #312G powder. The rabbit was euthanized with an overdose of anesthesic solution. The same procedure was used to demonstrate hemostatic effectiveness of formulation #312D (with sodium carbonate in place of calcium gluconate). Another similar demonstration was performed with #312G. However, in that case, bleeding of the transected spleen was stopped with the #312G powder formulation suspended in 12 gm of UCON LB-1715 (see above for description). It was concluded that dry carbomer formulations, and suspensions made with hydrophilic liquids, are effective and useful to arrest hemorrhage.

Example 7

To illustrate the nature of proposed hemostatic applications, any one of several carbomers can be used, without added alkaline salts, to illustrate how water activates such material to glue tissues together. Persons are asked to wet one thumb and first finger with tap water. A small amount (1-2 mm$^3$) of a carbomer powder is placed on the moistened finger. The person is asked to close the thumb on the first finger to hold the powder firmly for about 10 seconds. In most cases the polyacrylic acid becomes moistened enough to lightly glue the thumb and finger together. Alkaline salts are not required, but results of documented studies show that neutralized carbomers or transesterified polyvinyl alcohol gums exhibit improved adhesive strength, adhesion to tissues, and resistance to removal in the presence of excess water. However, it was concluded that an unadorned polymer provides a convenient demonstration to show how water from blood can activate hemostasis by forming an adhesive gum with a carbomer.

Example 8

U.S. Army requirements for combat casualty care have been defined as follows, ". . . a topical hemostatic agent must control rapidly flowing, otherwise lethal, large venous or arterial hemorrhage, through a pool of blood—without vascular control." These conditions were simulated as follows: A hot water bottle with an outlet tube (designed for delivery of an enema) was largely filled with warm water and suspended over a sink so that an attached 16 gauge needle (blunted) would be under at least three feet of water pressure following release of a valve. The needle was thrust through the outer surface of a fresh boneless chicken breast. The breast was arranged to have a concave surface, so the needle could deliver about 10 ml of water into the depression prior to overflow into the sink. One level tablespoonful (15 mm$^3$) of Carbopol 974P NF (a crosslinked poly(acrylic acid) product produced by Noveon, Inc., under CAS # 9003-01-4) powder was placed on the surface of a 3×3-inch, 12 ply, cotton gauze sponge. The sponge was placed on the sterile packaging envelope that had contained it. The water valve was opened so that an overflowing pool of water was established on the chicken breast. The envelope and sponge were inverted rapidly to deliver the powder directly over the needle tip, which was protruding slightly from the breast tissue in a horizontal plane. Indirect finger pressure (about 5-10 psi) was applied through the envelope and sponge for five minutes. No escaping water was detected during that period, so the water valve was closed. After five more minutes, a bolus of gummy material was peeled from the meat. A pink coating of meat fragments was observed on the contact surface of the material. The water bottle was refilled and the water valve was opened with the needle tip at the level of the bottom of a measuring cup. About 125 ml of water was collected during 60 seconds of flow.

The described procedure (with a different sponge assembly) was repeated with formulations composed of 15 mm$^3$ of 974P plus 2.5 mm$^3$ of calcium hydroxide, and 15 mm$^3$ of 974P with 5.0 mm$^3$ of calcium hydroxide. Both formulations completely prevented water flow but each was noticeably less strongly adherent to the chicken meat than 974P used alone. With 2.5 mm³ of calcium hydroxide, three small (3-5 mm diameter) pink patches were found on the contact face of the gel. With 5.0 mm 3 of calcium hydroxide, exothermia was detected in the fingers maintaining indirect pressure through 24 plies of sponge. No pink patches were found on the contact face of the gel, which was brittle enough to fracture when folded during removal. The procedure was repeated with 15 mm³ of 974P and 5 mm³ of light magnesium oxide. This formulation did not adhere to the chicken meat sufficiently well to totally prevent water flow when finger pressure was released. However restoration of moderate pressure with a water-filled measuring cup (about 6 pounds) stopped water flow as long as the cup was in place. A gelatinous gel was removed and found adherent to about half of the contact area. It was concluded that such a gel may provide effective and useful soft tissue splinting with minimal effort needed for surgical removal and/or lavage with electrolyte solutions.

The carbomer/salt formulations were spread on two 4×4-inch 12 ply sponges exposed by opening an 8×8 cm window in their sterile packaging envelope. This assembly was folded to permit one-hand delivery of the enclosed formulation (by release of the fold) directly over the embedded needle. It was concluded that the method of powder application could be improved if a film of polyacrylic acid could be used to confine a bolus of powder for more convenient delivery to a site of major hemorrhage. A thin layer of the 974P/MgO gel detached from the chicken breast was spread on aluminum foil. One ply of gauze sponge scrim was embedded in the gel. The gel was distributed evenly under a sheet of polyethylene film, which was then peeled off the layer of scrim and gel. After drying at about 40% relative humidity, the gel and scrim became constituted as a thin reinforced film. This results suggests that hemostatic powders with calcium salt content might be used to make films for calcium ion delivery (to the interface of hemostatic carbomer and blood) to aid fibrin-based clotting and precise delivery of the powder. It was concluded that the described results with chicken breasts support use of anethetized live animals to confirm the apparent potential of methods and formulations of the invention to arrest otherwise fatal hemorrhage.

Example 9

In veterinary practice, it is not uncommon to clip canine toenails more closely than is desirable. This results in bleeding from the severed core of the nail. This is difficult to control because the nail prevents use of a hemostat for vascular control. Arrangements were made with a practicing veterinarian to try a carbomer formulation on bleeding nails. Three parts of CARBOPOL 974P (see above for description) and one part of calcium polycarbophil, USP (v/v) were worked together with a spatula. This composition is equivalent to a ratio of seven parts CARBOPOL 974P (see above for description) to five parts of calcium polycarbophil, USP (w/w). The practicing veterinarian has reported that this mixture is very effective in control of toenail bleeding. It was concluded that this clinical report supports investigation of other veterinary applications of the methods and formulations of the invention.

All references mentioned herein are incorporated in their entirety by reference.

What is claimed:

1. A method for forming a bioadhesive aqueous gel or mucilage to effect a rapid hemostatic response and control hemorrhage and fluid loss from an open wound, denuded tissue, or burned skin,
   comprising the steps of
   (i) applying to the open wound, denuded tissue or burned skin an anhydrous gel-forming polymer or polymer composition selected from the group consisting of
   (a) a carbomer having the structural formula $[CH_2=CHCO_2H]_n$, where n is between 10,000 and 70,000,
   (b) a composition consisting essentially of a carbomer having the structural formula $[CH_2=CHCO_2H]_n$, where n is between 10,000 and 70,000, and a desiccated water soluble organic or inorganic base,
   (c) a composition consisting essentially of a carbomer having the structural formula $[CH_2=CHCO_2H]_n$, where n is between 10,000 and 70,000, and a desiccated basic salt and
   (ii) allowing water present in blood or other body fluid at the site of the open wound, denuded tissue, or burned skin to activate an ionization reaction in situ with the carbomer of (a), (b), or (c) thereby forming an aqueous gel or mucilage having sufficient viscosity and bioadhesiveness to cover and adhere to the open wound, denuded tissue, or burned skin so that a rapid hemostatic response is effected and hemorrhage and fluid loss is controlled.

2. The method of claim 1, wherein the carbomer comprises strands that are cross-linked by divalent ions.

3. The method of claim 1, wherein in composition (b) the carbomer and the water soluble organic or inorganic base are admixed to form a water mucilage or gel with a viscosity that increases with pH in the range between about 4 and about 8.

4. The method of claim 1, wherein in composition (c) the desiccated basic salt is selected from the group consisting of calcium hydroxide, calcium carbonate, magnesium hydroxide, sodium carbonate, dibasic sodium phosphate, and low density magnesium oxide.

5. The method of claim 1, wherein in composition (c) the desiccated basic salt provides divalent cations that ionically crosslink polymer strands and increase mucilage viscosities to greater degree than monovalent cations.

6. The method of claim 5, wherein the divalent cations are selected from the group consisting of $Ca^{++}$ and $Mg^{++}$.

7. The method of claim 1, wherein step (i) further includes applying to the open wound, denuded tissue or burned skin at least one calcium salt, and a desiccated vasoconstrictive drug.

8. The method of claim 7, wherein the calcium salt is soluble and has a metabolizable anion.

9. The method of claim 7, wherein the desiccated vasoconstrictive drug is L epinephrine tartrate.

10. The method of claim 1, which comprises the further step of applying to the open wound, denuded tissue or burned skin therapeutic substances incorporated as anhydrous soluble drugs that become dissolved in water from the tissue and diffuse into the tissues from the mucilage to serve as
   (a) antimicrobial agents,
   (b) anti-inflammation agents
   (c) agents that resist apoptosis, or
   (d) agents that preserve cellular functions.

11. The method of claim 10, wherein the antimicrobial agents are selected from the group consisting of antibiotics and sulfonamides.

12. The method of claim 10, wherein the anti-inflammation agents, the agents that resist apoptosis, and the agents that preserve cellular functions are selected from the group consisting of antioxidants and nutrients.

13. The method of claim 1, wherein the polymer further protects the open wound, denuded tissue or burned skin from loss of body substances selected from the group consisting of water, blood, plasma, serum, proteins, electrolytes and nutrients.

14. The method of claim 1, wherein the polymer provides a barrier to protect the open wound, denuded tissue or burned skin from access by and further damage by substances selected from the group consisting of oxygen, dirt, foreign protein antigens, foreign organisms, pathogens and saprophytes.

15. The method of claim 1, wherein the polymer provides a protective shield that limits development of fibroblastic tissue and supports epithelialization.

16. The method of claim 1, wherein the polymer provides a barrier to protect the open wound, denuded tissue or burned skin from access by and further damage by chemical warfare agents, biological warfare agents, and/or noxious industrial substances.

17. The method of claim 1, which comprises the further step of applying pressure to the site.

18. The method of claim 1, wherein the polymer is present on or in a woven or non-woven fabric.

19. The method of claim 1, which comprises the further step of adding water to the outside surface of the polymer during gelling or after gelling occurs.

20. The method of claim 1, wherein the polymer is in the form of an anhydrous powder.

21. The method of claim 1, wherein the polymer is suspended in a desiccated hydrophilic liquid.

22. A method for forming a bioadhesive aqueous gel or mucilage to effect a rapid hemostatic response and control hemorrhage and fluid loss from an open wound, denuded tissue, or burned skin,
    comprising the steps of
    (i) applying to the open wound, denuded tissue or burned skin an anhydrous gel-forming polymer composition consisting of
    a carbomer having the structural formula $[CH_2=CHCO_2H]_n$, where n is between 10,000 and 70,000,
    a non-corrosive alkaline salt capable of neutralizing acidic sites of the carbomer,
    an anhydrous hydrophilic liquid, in which the carbomer and the alkaline salt are suspended and which permits the carbomer to form a gel in the presence of water, and one or more of an antibiotic, blood-clotting enzymes, decontaminating reagents, detoxifiers, camouflage pigment, pH indicators, vasoconstrictive agents, agents capable of detecting the presence of toxic or infectious compounds, starch, sodium borate, calcium hydroxide, calcium gluconate, magnesium oxide and borax, and
    (ii) allowing water present in blood or other body fluid at the site of the open wound, denuded tissue, or burned skin to activate an ionization reaction in situ with the carbomer thereby forming an aqueous gel or mucilage having sufficient viscosity and bioadhesiveness to cover and adhere to the open wound, denuded tissue, or burned skin so that a rapid hemostatic response is effected and hemorrhage and fluid loss is controlled.

23. The method of claim 22, wherein the anhydrous hydrophilic liquid is selected from the group consisting of polyoxyalkylene glycol and nitrile silicone fluid.

24. A method for forming a bioadhesive artificial scab on an open wound, denuded tissue, or burned skin, comprising the step of applying to the open wound, denuded tissue or burned skin an anhydrous gel-forming polymer or polymer composition selected from the group consisting of
    (a) a carbomer having the structural formula $[CH_2=CHCO_2H]_n$, where n is between 10,000 and 70,000,
    (b) a composition consisting essentially of a carbomer having the structural formula $[CH_2=CHCO_2H]_n$, where n is between 10,000 and 70,000, and a desiccated water soluble organic or inorganic base,
    (c) a composition consisting essentially of a carbomer having the structural formula $[CH_2=CHCO_2H]_n$, where n is between 10,000 and 70,000, and a desiccated basic salt and
    wherein when the anhydrous gel-forming polymer or polymer composition is applied to the open wound, denuded tissue, or burned skin and contacts water present in blood or other body fluid therein, an ionization reaction is activated in situ with the carbomer of (a), (b), or (c) thereby forming an aqueous gel or mucilage having sufficient viscosity and bioadhesiveness to cover and adhere to the open wound, denuded tissue, or burned skin so that a rapid hemostatic response is effected, and an artificial scab is thereafter formed.

25. The method of claim 1, wherein the carbomer of (a), (b), and (c) is cross-linked to form three-dimensional structures.

26. The method of claim 24, wherein the carbomer of (a), (b), and (c) is cross-linked to form three-dimensional structures.

27. The method of claim 1, wherein the carbomer is cross-linked with allyl sucrose.

28. The method of claim 24, wherein the carbomer is cross-linked with allyl sucrose.

29. The method of claim 24, wherein in composition (b) the carbomer and the water soluble organic or inorganic base are admixed to form a water mucilage or gel with a viscosity that increases with pH in the range between about 4 and about 8.

30. The method of claim 24, wherein in composition (c) the desiccated basic salt is selected from the group consisting of calcium hydroxide, calcium carbonate, magnesium hydroxide, sodium carbonate, dibasic sodium phosphate, and low density magnesium oxide.

31. The method of claim 24, wherein in composition (c) the desiccated basic salt provides divalent cations that ionically crosslink polymer strands and increase mucilage viscosities to greater degree than monovalent cations.

32. The method of claim 24, wherein the divalent cations are selected from the group consisting of $Ca^{++}$ and $Mg^{++}$.

33. The method of claim 24, which comprises the further step of applying to the open wound, denuded tissue or burned skin therapeutic substances incorporated as anhydrous soluble drugs that become dissolved in water from the tissue and diffuse into the tissues from the mucilage to serve as
    (e) antimicrobial agents,
    (f) anti-inflammation agents
    (g) agents that resist apoptosis, or
    (h) agents that preserve cellular functions.

34. The method of claim 33, wherein the antimicrobial agents are selected from the group consisting of antibiotics and sulfonamides.

35. The method of claim 33, wherein the anti-inflammation agents, the agents that resist apoptosis, and the agents that preserve cellular functions are selected from the group consisting of antioxidants and nutrients.

36. The method of claim 24, wherein the polymer further protects the open wound, denuded tissue or burned skin from loss of body substances selected from the group consisting of water, blood, plasma, serum, proteins, electrolytes and nutrients.

37. The method of claim 24, wherein the polymer provides a barrier to protect the open wound, denuded tissue or burned skin from access by and further damage by substances selected from the group consisting of oxygen, dirt, foreign protein antigens, foreign organisms, pathogens and saprophytes.

38. The method of claim 24, wherein the polymer provides a protective shield that limits development of fibroblastic tissue and supports epithelialization.

39. The method of claim 24, wherein the polymer provides a barrier to protect the open wound, denuded tissue or burned skin from access by and further damage by chemical warfare agents, biological warfare agents, and/or noxious industrial substances.

40. The method of claim 24, which comprises the further step of adding water to the outside surface of the polymer during gelling or after gelling occurs.

41. The method of claim 24, wherein the polymer is in the form of an anhydrous powder.

42. The method of claim 24, wherein the polymer is suspended in a desiccated hydrophilic liquid.

43. A method for forming a bioadhesive artificial scab on an open wound, denuded tissue, or burned skin,
comprising the steps of
(i) applying to the open wound, denuded tissue or burned skin an anhydrous gel-forming polymer composition consisting of
a carbomer having the structural formula $[CH_2\!=\!CHCO_2H]_n$, where n is between 10,000 and 70,000,
a non-corrosive alkaline salt capable of neutralizing acidic sites of the carbomer,
an anhydrous hydrophilic liquid, in which the carbomer and the alkaline salt are suspended and which permits the carbomer to form a gel in the presence of water, and one or more of an antibiotic, blood-clotting enzymes, decontaminating reagents, detoxifiers, camouflage pigment, pH indicators, vasoconstrictive agents, agents capable of detecting the presence of toxic or infectious compounds, starch, sodium borate, calcium hydroxide, calcium gluconate, magnesium oxide and borax, and
(ii) allowing water present in blood or other body fluid at the site of the open wound, denuded tissue, or burned skin to activate an ionization reaction in situ with the carbomer thereby forming an aqueous gel or mucilage having sufficient viscosity and bioadhesiveness to cover and adhere to the open wound, denuded tissue, or burned skin so that a rapid hemostatic response is effected and hemorrhage and fluid loss is controlled.

44. The method of claim 43, wherein the anhydrous hydrophilic liquid is selected from the group consisting of polyoxyalkylene glycol and nitrile silicone fluid.

* * * * *